(12) United States Patent
Rodi

(10) Patent No.: US 6,272,771 B1
(45) Date of Patent: Aug. 14, 2001

(54) TOE PROTECTION DEVICE FOR ORTHOPEDIC FOOT SUPPORTS

(76) Inventor: Kathleen L. Rodi, 77 Lake Shore Dr., Boardman, OH (US) 44511

( * ) Notice: Subject to any disclaimer, the term of this patent is extended or adjusted under 35 U.S.C. 154(b) by 0 days.

(21) Appl. No.: 09/573,954

(22) Filed: May 19, 2000

(51) Int. Cl.[7] ............................ A43C 13/14; A43B 13/22
(52) U.S. Cl. .............................. 36/77 R; 36/72 R; 36/110
(58) Field of Search .................................. 36/77 R, 72 R, 36/110; 602/11

(56) References Cited

U.S. PATENT DOCUMENTS

| | | | |
|---|---|---|---|
| 1,626,489 | * 4/1927 | Wojcik | 36/77 R |
| 2,661,547 | * 12/1953 | Hyde et al. | 36/72 R |
| 3,410,007 | * 11/1968 | Peterson | 36/77 R |
| 3,487,830 | 1/1970 | Pruett . | |
| 3,773,041 | 11/1973 | Bogar, Jr. et al. . | |
| 4,061,138 | 12/1977 | Bernstein . | |
| 4,177,583 | * 12/1979 | Chapman | 36/110 |
| 4,454,872 | 6/1984 | Brouhard . | |
| 5,778,565 | * 7/1998 | Holt et al. | 36/77 R |
| 5,809,666 | * 9/1998 | Harwood | 36/77 R |

* cited by examiner

Primary Examiner—M. D. Patterson
(74) Attorney, Agent, or Firm—Harpman & Harpman

(57) ABSTRACT

A toe protector for orthopedic foot fixtures comprising a semi-rigid arcuate enclosure that is positioned over a patient's exposed toes extending from within a fabric foot fixture. The toe protector overlies the exposed toes and is secured in place by engagement with portions of the foot fixture.

4 Claims, 4 Drawing Sheets

TOE PROTECTION DEVICE FOR ORTHOPEDIC FOOT SUPPORTS

BACKGROUND OF THE INVENTION

1. Technical Field

This invention relates to foot supports and braces that are used on a patient's foot for immobilization and support after injury. More specifically this invention is directed to toe protection devices that are used in conjunction with these supports to protect the exposed toes extending from the foot enclosure.

2. Description of Prior Art

A number of prior art devices have been developed in an attempt to address the problem of exposed toes evident with the use of the typical foot cast or other fabric foot ankle support structures. Heretofore such devices have utilized protection bars that encircle around the toes and are secured to the cast, see for example U.S. Pat. No. 4,554,872 which has a horizontally disposed rigid band that extends along opposite sides of the foot and wraps around in spaced relation to the patient's toes.

Alternately, in U.S. Pat. No. 3,773,041 a toe guard is described for a walking cast that extends around the toe utilizing a horizontal band that extends from a central support stem engaged under the cast.

A toe protection sock is seen in U.S. Pat. No. 3,487,830 in which a fabric cap member is fitted over the ends of the exposed toes and cast. This device is held in place by a pair of restraining straps that extend around the outer surface of the cast.

In U.S. Pat. No. 4,061,138 a toe protection and foot support for an orthopedic cast is disclosed having an elongated support tongue extending from under the patient's foot with a toe dome shaped toe cover inter-engaged on a mounting rim extending around the forward end of the support.

SUMMARY OF THE INVENTION

A toe protection device for use with orthopedic foot fixtures and casts and orthopedic fabric foot and ankle braces. The toe protection device overlies the patient's exposed toes that typically extend from the end of the orthopedic enclosures. The toe protection device is of a contoured arcuate configuration that extends over the toes and is held in place by engagement with portions of the enclosing device.

DESCRIPTION OF THE PREFERRED EMBODIMENT

Figure 1:
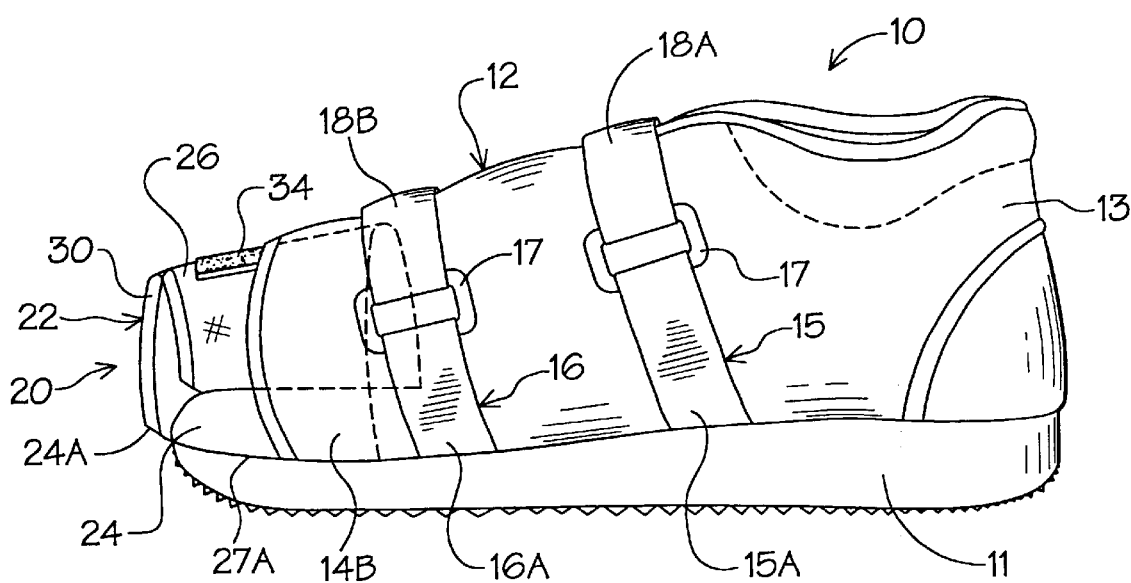
FIG. 1 is a side elevational view of an orthopedic foot support with a toe protector of the invention positioned within.

Referring now to FIG. 1 of the drawings, a therapeutic fabric foot enclosure 10 can be seen having a resilient sole 11 with an integral fabric foot engagement portion 12 extending therefrom. The foot engagement portion 12 has a heel area 13 and a pair of oppositely disposed flexible fabric closure flaps 14A and 14B extending from over the length of the sole 11. A pair of strap assemblies 15 and 16 extend from the sole 11 and overlie the respective flaps 14A and 14B and are in spaced longitudinal relation to one another. Each of the strap assemblies 15 and 16 comprises a pair of straps 15A & 15B and 16A & 16B with attached buckle fittings 17. Engagement straps 18A & 18B extend between the respective buckle fittings 17 of each of the strap pairs and have hook and loop fastening elements generally indicated at 19 on the respective sides so as to be secured to themselves after passing through the respective oppositely disposed buckle fittings 17 of the respective strap pairs 15A & 15B and 16A & 16B as will be well know by those skilled in the art as best seen in FIGS. 1–5 of the drawings.

Figure 2:
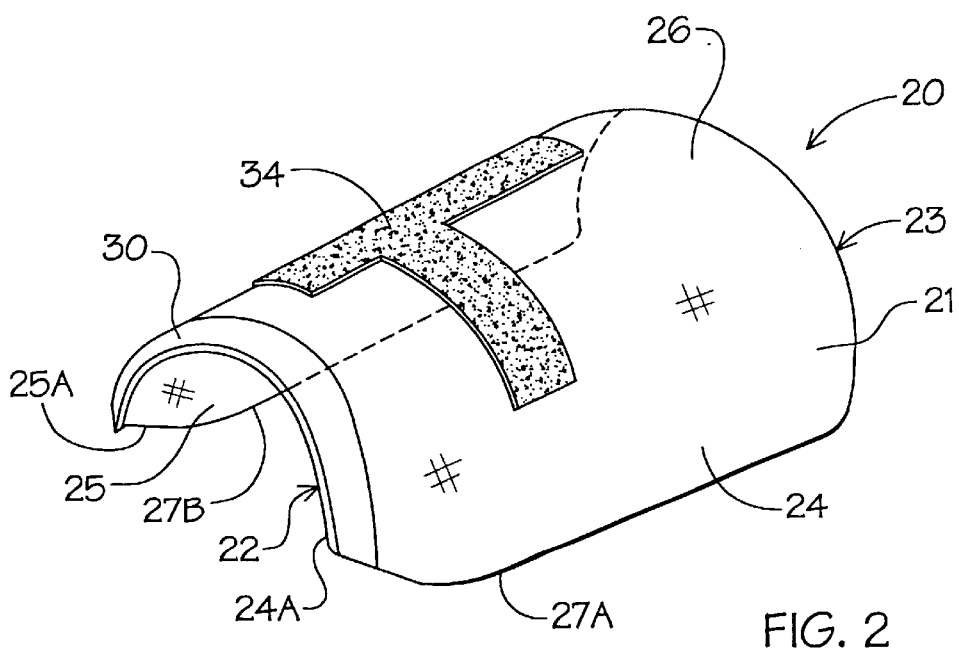
FIG. 2 is a perspective view of the toe protector of the invention.
Figure 3:
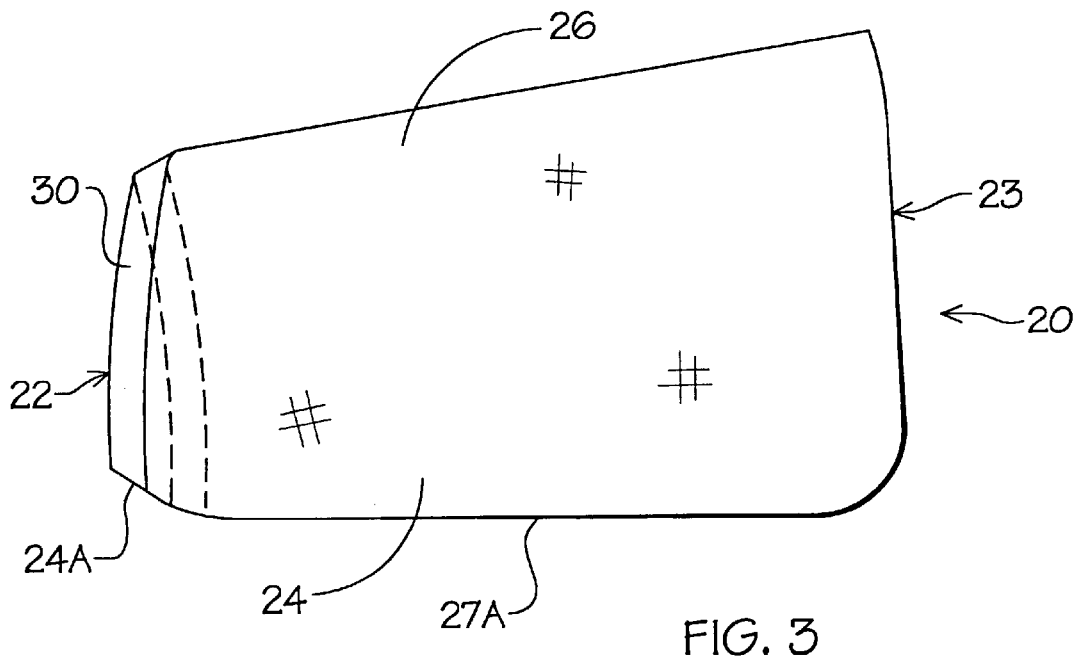
FIG. 3 is a side elevational view of the toe protector of the invention.

A toe protection device 20 of the invention has an elongated arcuate main body member 21 formed from flexible synthetic resin material, best seen in FIGS. 2 and 3 of the drawings. The main body member 21 defines a toe opening 22 at one end and a foot opening 23 at its oppositely disposed end.

The elongated arcuate main body 21 defines respective side elements 24 and 25 with an integral interengaging interconnecting top portion 26.

Each of the side elements 24 and 25 have respective sole engagement edges 27A and 27B with curved transitional corners 24A and 25A defining the toe opening 22. The main body member 21 is tapered longitudinally from the foot opening 23 downwardly to the toe opening 22 as best seen in FIG. 3 of the drawings. A portion of the main body member 21 that extends inwardly from a perimeter edge along the toe opening is recessed at 30.

Figure 4:
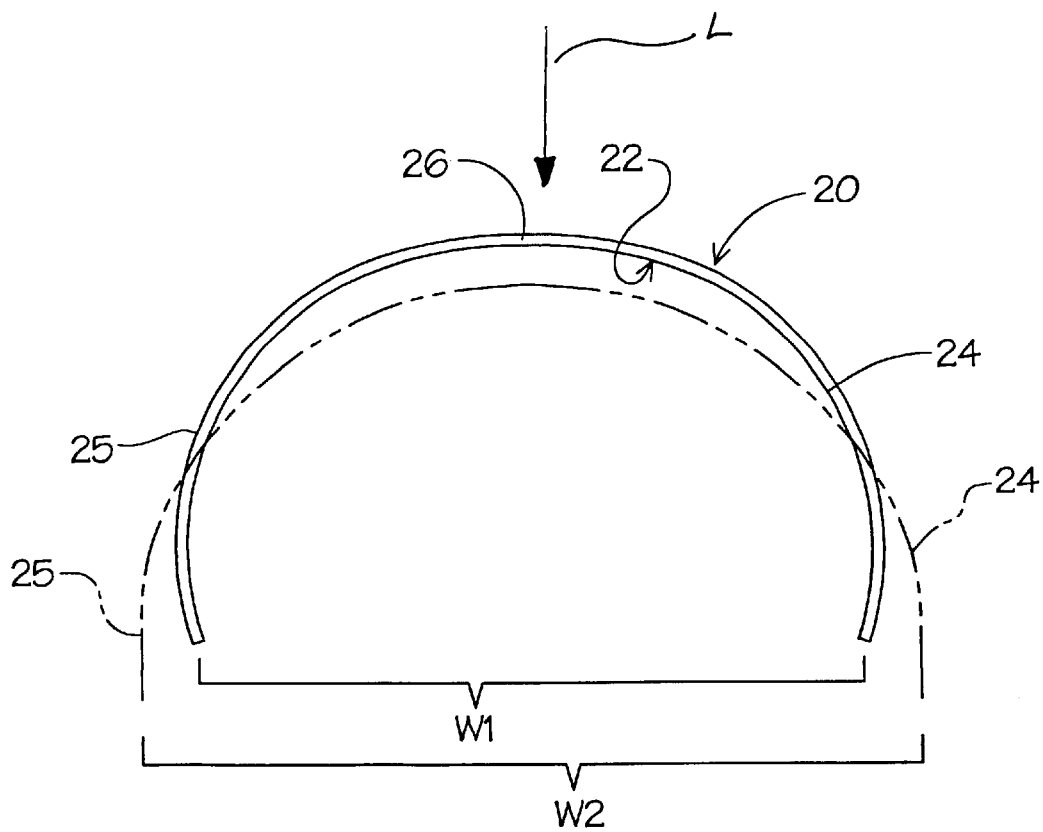
FIG. 4 is an illustrative end view.

Referring now to FIG. 4 of the drawings, the toe protection device 20 of the invention can be seen having a cross-sectionally thin configuration so as to impart an adjustable transverse flexation when depressed as from a vertical load indicating by arrow L from an initial rest configuration shown in solid lines to a deflective position shown in broken lines. The deflection property thus imparted will allow for adjustability to the various sole widths indicated by a minimum range at W1 to a maximum range at W2.

Figure 5:
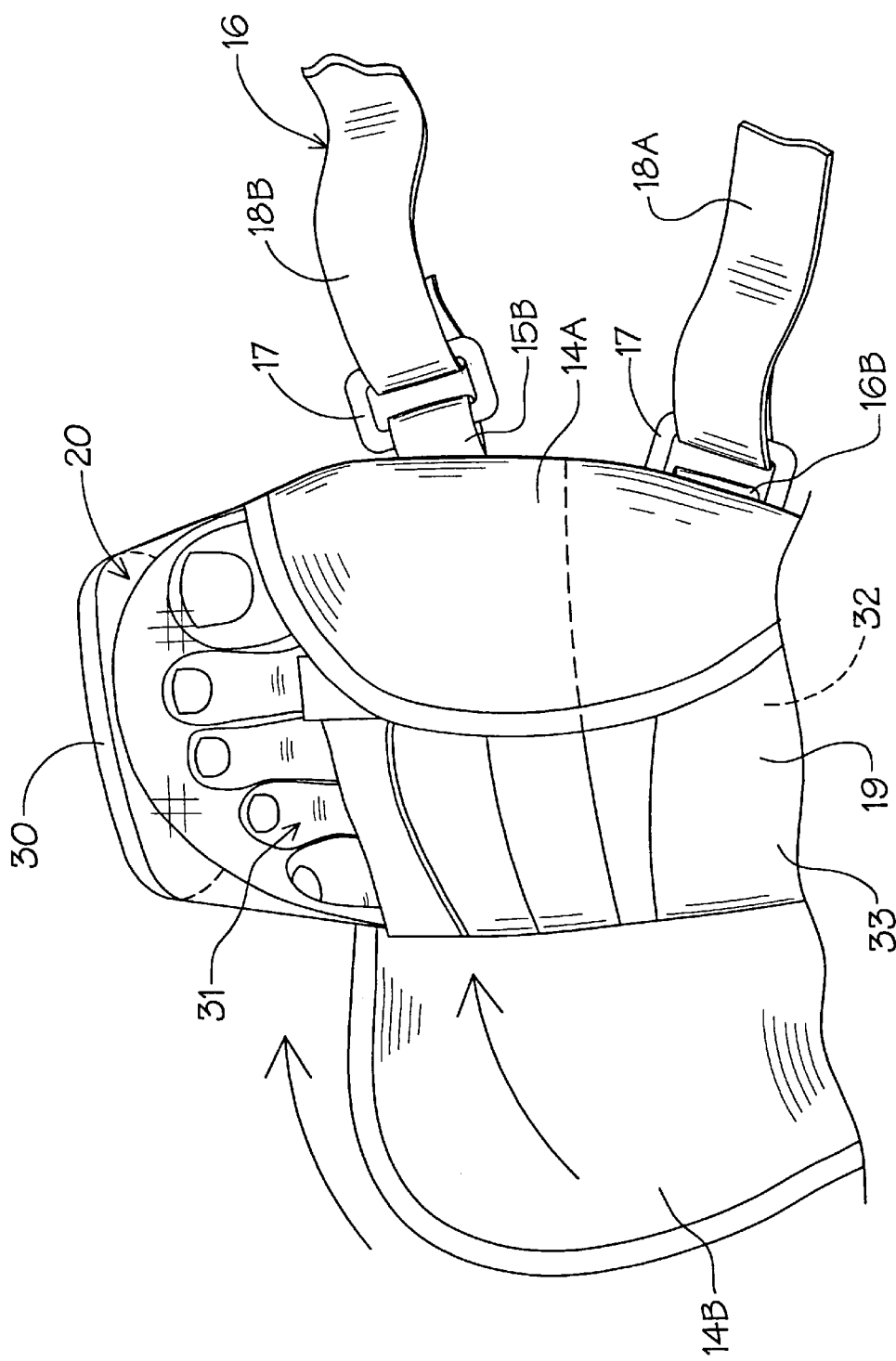
FIG. 5 is a partial top plan view of a foot support enclosure in open position with the toe protector of the invention positioned within.
Figure 6:
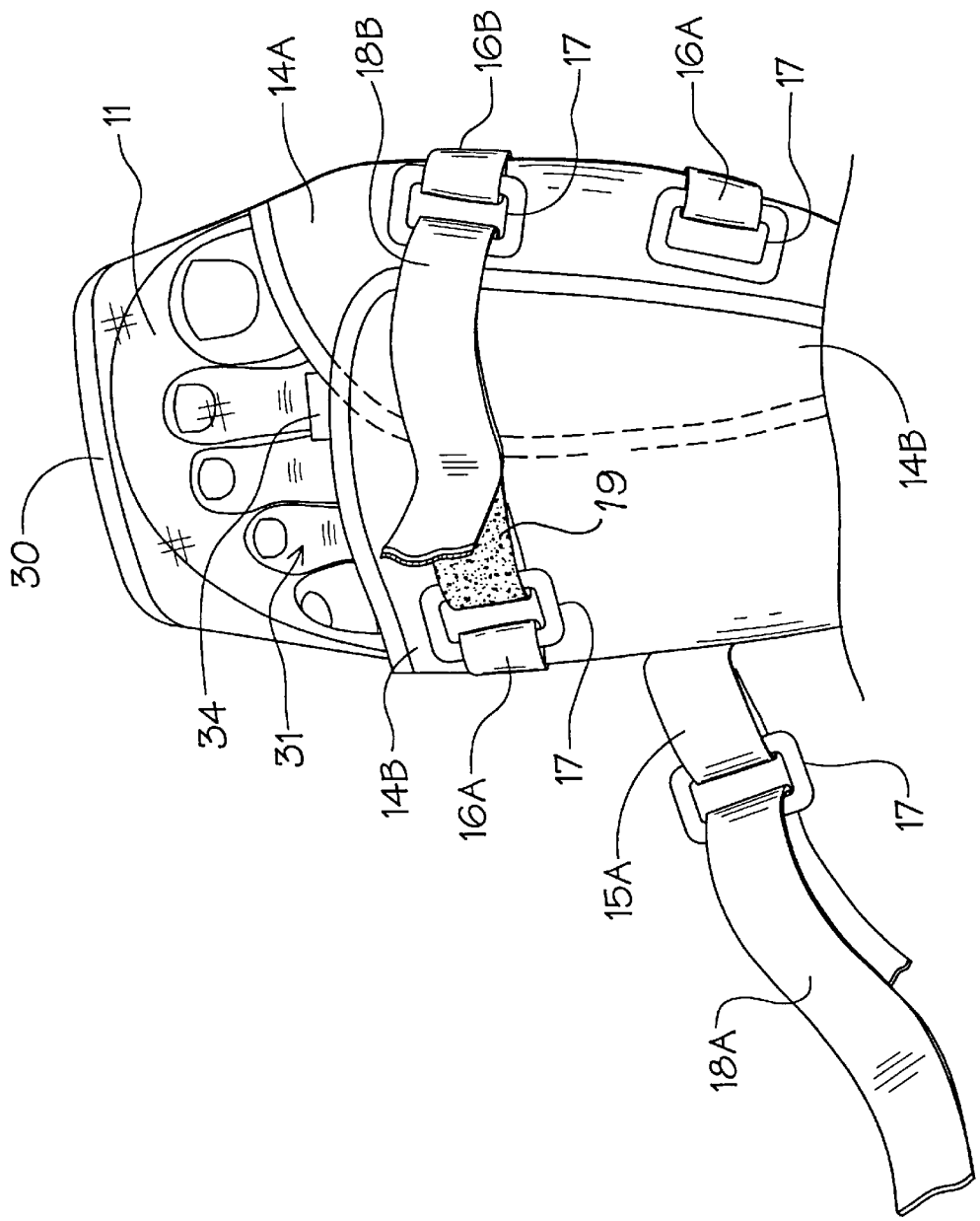
FIG. 6 is a partial top plan view of the foot enclosure set forth in FIG. 5 in closed position over a fully engaged toe protector of the invention.

Referring now to FIGS. 5 and 6 of the drawings, in use, the toe protector 20 is positioned over a patient's toes 31 extending from the patient's foot 32. Typically, the foot 32 has been wrapped in a protective fabric stocking or band 33 with the toes 31 normally exposed. The toe protective device 20 is removably secured in position by engagement with the overlapping flaps 14A and 14B by a strip of hook attachment material 34 of commercially available hook and loop material known as Velcro which is adhesively secured to the upper portion 26 of the toe protector 20. The hook attachment material 34 can extend longitudinally or transversely across the upper portion 26 depending on the application of choice and for illustration purposes both positions are shown in FIG. 2 of the drawings.

In this example, flap 14A engages the toe protection device 21, then flap 14B overlies flap 14A indicated by directional arrows in FIG. 5 of the drawings. The strap assemblies 15 and 16 are secured over the closed flaps and secured thereover as will be well understood by those skilled in the art.

It will be evident that a portion of the toe protector 20 extending out from beyond the enclosed fabric foot support, shielding the hereinbefore exposed toes from accidental contact with foreign objects.

The toe protector 20 as noted is made of synthetic resin material and is illustrated as being transparent in this example chosen for illustration.

It will be apparent that given the toe protector 20's transverse adjustability and longitudinally tapered configuration that it can be adjustably positioned within various therapeutic foot enclosures where the patient's toe extends unprotected therefrom.

It will thus be seen that a new and novel toe protection device has been illustrated and described and it will be apparent to those skilled in the art that various changes and modifications may be made therein without departing from the spirit of the invention, therefore I claim:

1. The toe protection device for use with orthopedic foot supports comprises, a one-piece elongated arcuate body member, said body member having oppositely disposed side portions and an integral top portion extending therebetween, said body member defining a toe opening and an oppositely disposed foot opening, said side portions define linear sole engagement edges, said body member being longitudinally tapered from said foot opening to said toe opening, a recessed portion extending inwardly from the perimeter edge along the toe opening, means for removably securing said toe protector within said orthopedic foot support, and means for transverse dimensional adjustment of said side portion of said toe protector.

2. The toe protection device set forth in claim 1 wherein said toe protector is made of a synthetic resin material.

3. The toe protection device set forth in claim 1 wherein said means for removably securing said toe protector within said orthopedic foot support comprises, elongated strips of fastening material secured to said toe protector's top portion so as to be engaged by overlapping portions of said orthopedic foot support.

4. A toe protection device set forth in claim 1 wherein said means for transverse dimensional adjustment of said side portions from a known first position at rest to multiple intermediate positions greater than that of said known first positions comprises, a deformable cross-sectional dimension of said main body member in relation to vertical load input by redilineation of said side linear engagement edges in spaced relation to one another.

\* \* \* \* \*